United States Patent
Khuri-Yakub et al.

(10) Patent No.: US 7,305,883 B2
(45) Date of Patent: Dec. 11, 2007

(54) CHEMICAL MICROMACHINED MICROSENSORS

(75) Inventors: Butrus T. Khuri-Yakub, Palo Alto, CA (US); Calvin F. Quate, Menlo Park, CA (US); James K. Gimzewski, Santa Monica, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/543,550

(22) Filed: Oct. 4, 2006

(65) Prior Publication Data

US 2007/0089516 A1    Apr. 26, 2007

Related U.S. Application Data

(60) Provisional application No. 60/724,075, filed on Oct. 5, 2005.

(51) Int. Cl.
  *G01N 29/036* (2006.01)
(52) U.S. Cl. .................. 73/579; 73/597; 73/862.41
(58) Field of Classification Search ............. 73/579, 73/597, 862.41, 861.18, 861.31, 642, 644, 73/632
  See application file for complete search history.

(56) References Cited

U.S. PATENT DOCUMENTS

| 5,583,290 A * | 12/1996 | Lewis ................. 73/514.18 |
| 6,567,572 B2 * | 5/2003 | Degertekin et al. ........... 385/12 |
| 6,650,204 B2 * | 11/2003 | Ma et al. .................. 333/188 |
| 6,854,338 B2 | 2/2005 | Khuri-Yakub et al. |
| 7,023,065 B2 * | 4/2006 | Ayazi et al. .............. 257/414 |
| 2004/0197227 A1 | 10/2004 | Hauan et al. |
| 2004/0236223 A1 | 11/2004 | Barnes et al. |
| 2005/0005676 A1 | 1/2005 | Crawley et al. |
| 2005/0146247 A1 | 7/2005 | Fisher et al. |
| 2005/0200241 A1 | 9/2005 | Degertekin |
| 2006/0078473 A1 | 4/2006 | Murakami |
| 2006/0116585 A1 * | 6/2006 | Nguyen-Dinh et al. ..... 600/459 |
| 2007/0059858 A1 * | 3/2007 | Caronti et al. ............ 438/50 |

OTHER PUBLICATIONS

Oralkan et al., IEEE Trans. on UFFC 49, No. 11, 1596-610 (Nov. 2002).
Baller et al. Ultramicroscopy 2000, 82, 1-9.
Battiston et al. Sensors and Actuators B-Chemical 2001, 77, 122-131.

* cited by examiner

*Primary Examiner*—Hezron Williams
*Assistant Examiner*—Jacques M. Saint-Surin
(74) *Attorney, Agent, or Firm*—Lumen Intellectual Property Services, Inc.

(57) ABSTRACT

The present invention provides sensors based on micromachined ultrasonic transducer technology. The sensors preferably include a plurality of sensor elements, but may include only one sensor element. Arrays of sensors are also provided. Sensor elements include a functionalized membrane supported over a substrate by a support frame. The functionalized membrane, support frame and substrate together form a vacuum gap. The sensor element is connected to an electrical circuit, which is configured to operate the sensor element at or near an open circuit resonance condition. The mechanical resonance frequency of the functionalized membrane is responsive to binding of an agent to the membrane. Thus, the sensor element also includes a detector, where the detector provides a sensor output responsive to the mechanical resonance frequency of the sensor element.

21 Claims, 9 Drawing Sheets

CHEMICAL MICROMACHINED MICROSENSORS

CROSS-REFERENCE TO RELATED APPLICATIONS

This application claims priority from U.S. Provisional Patent Application No. 60/724,075, filed Oct. 5, 2005, which is incorporated herein by reference.

FIELD OF THE INVENTION

The present invention relates generally to sensing devices. More specifically, it relates to sensing devices employing chemically functionalized micromachined sensor elements.

BACKGROUND

Resonant sensors depend on target molecules adsorbed in the sensing material to change properties that are reflected in the resonance frequency. A wide variety of cantilever, membrane and piezoelectric resonator-based sensors have been fabricated using MEMS technology. These sensors generally detect agents through the use of polymer films and coatings with selective adsorption for a specific agent or set of agents. Although these sensors provide a certain degree of sensitivity, it is desirable in many applications to have sensors with even higher sensitivities.

A capacitive micromachined ultrasonic transducer (cMUT) is a micromachined device having a substrate and a membrane supported above the substrate by an insulating material. A variable voltage applied between the substrate and membrane drives the membrane to vibrate and emit sound waves at ultrasonic frequencies. Arrays of cMUTs have been used for transmitting and receiving ultrasonic beam patterns in air and water over a frequency range from 10 kHz to 100 MHz. These cMUTs rely on the very large electric field ($E > 10^8$ V/m) in the gap of the capacitor to provide an electromechanical coupling coefficient close to unity.

cMUTs are mostly used for medical imaging. In addition, they have been used to indirectly measure various fluid characteristics, based on processing of ultrasonic signals transmitted and received through the fluid. In current cMUT devices and applications, the cMUT elements are used to transmit and/or receive ultrasonic energy between the cMUT element and the environment. Moreover, to ensure reliable and consistent operation, cMUT element membranes are normally designed to be non-reactive to chemicals, light, and other environmental factors that may alter or interfere with their operational characteristics. However, due to their resonant character, cMUT devices have the potential to be used as sensors, in a manner similar to MEMS cantilever, membrane, and piezoelectric resonator-based sensors. Accordingly, there is a need in the art to develop sensors based on cMUT technology.

SUMMARY OF THE INVENTION

The present invention provides sensors based on micromachined ultrasonic transducer technology. The sensors preferably include a plurality of sensor elements, but may include only one sensor element. In one embodiment, each of these sensor elements includes a functionalized membrane and a substrate. Sensor elements further include a support frame that, together with the substrate and functionalized membrane, defines a vacuum gap. The sensor elements are connected to a detector, which provides a sensor output responsive to a mechanical resonance frequency of the sensor element. The sensor output may be responsive to both a fundamental mode and harmonics of the mechanical resonance frequency. The mechanical resonance frequency is in turn responsive to binding of an agent to the functionalized membrane. The sensor elements further include an electrical circuit, where the electrical circuit is configured to operate the sensor element at or near an open circuit resonance condition. In sensors according to this embodiment, changes in mechanical resonance frequency may be detected by an optical detector, a magnetic detector, a mechanical stress detector, or a capacitance detector.

In another embodiment, each sensor element contains a functionalized membrane including a first electrode and a substrate including a second electrode, where the first and second electrodes define a capacitor. Each sensor element further includes a support frame, where the support frame, functionalized membrane and substrate define a vacuum gap. In this embodiment, the sensor element also includes an electrical circuit including the capacitor, where the electrical circuit provides a sensor output responsive to a mechanical resonance frequency of the sensor element. The sensor output may be responsive to both a fundamental mode and harmonics of the mechanical resonance frequency. The mechanical resonance frequency is responsive to binding of an agent to the functionalized membrane. The electrical circuit is configured to operate the sensor element at or near an open circuit resonance condition. Thus, the electrical circuit preferably further includes a source of DC bias.

Sensors according to the present invention preferably operate at a frequency greater than about 1 MHz, more preferably between about 1 MHz and about 100 MHz. In addition, the sensors preferably have a Q factor of at least about 50. Sensor elements preferably have a vacuum gap of between about 0.1 μm and about 5 μm in height. Sensors according to the present invention may operate in a gaseous or liquid environment, but preferably operate in a gaseous environment, e.g. air.

Preferably, membranes according to the present invention are made of silicon and are functionalized with a polymer gel matrix. Different sensor elements may be functionalized with the same or a different chemistry.

In a preferred embodiment, sensors also include a plurality of reference elements. Reference elements preferably include an unfunctionalized membrane including a first electrode and a substrate including a second electrode, where the first and second electrodes define a capacitor. Reference elements also include a support frame, where the support frame, unfunctionalized membrane and substrate define a vacuum gap. Reference elements further include an electrical circuit including the capacitor, where the electrical circuit provides a reference output responsive to a mechanical resonance frequency. The electrical circuit is configured to operate the reference element at or near an open circuit resonance condition. In the case where a non-capacitive sensor is used, the reference element would not include electrodes and would instead include a detector to, e.g. optically, piezoelectrically, or magnetically detect the mechanical resonance frequency of the reference element. In either case, the reference elements may be configured to operate at a same or different mechanical resonance frequency of at least one of the sensor elements.

The sensor may further include a source of heating the sensor element. In this case, the electrical circuit would further provide a sensor output responsive to thermal desorption of bound agent from the functionalized membrane.

BRIEF DESCRIPTION OF THE FIGURES

The present invention together with its objectives and advantages will be understood by reading the following description in conjunction with the drawings, in which.

TABLE 1 shows parameters of membranes for two sensor designs.

DETAILED DESCRIPTION OF THE INVENTION

Figure 1:
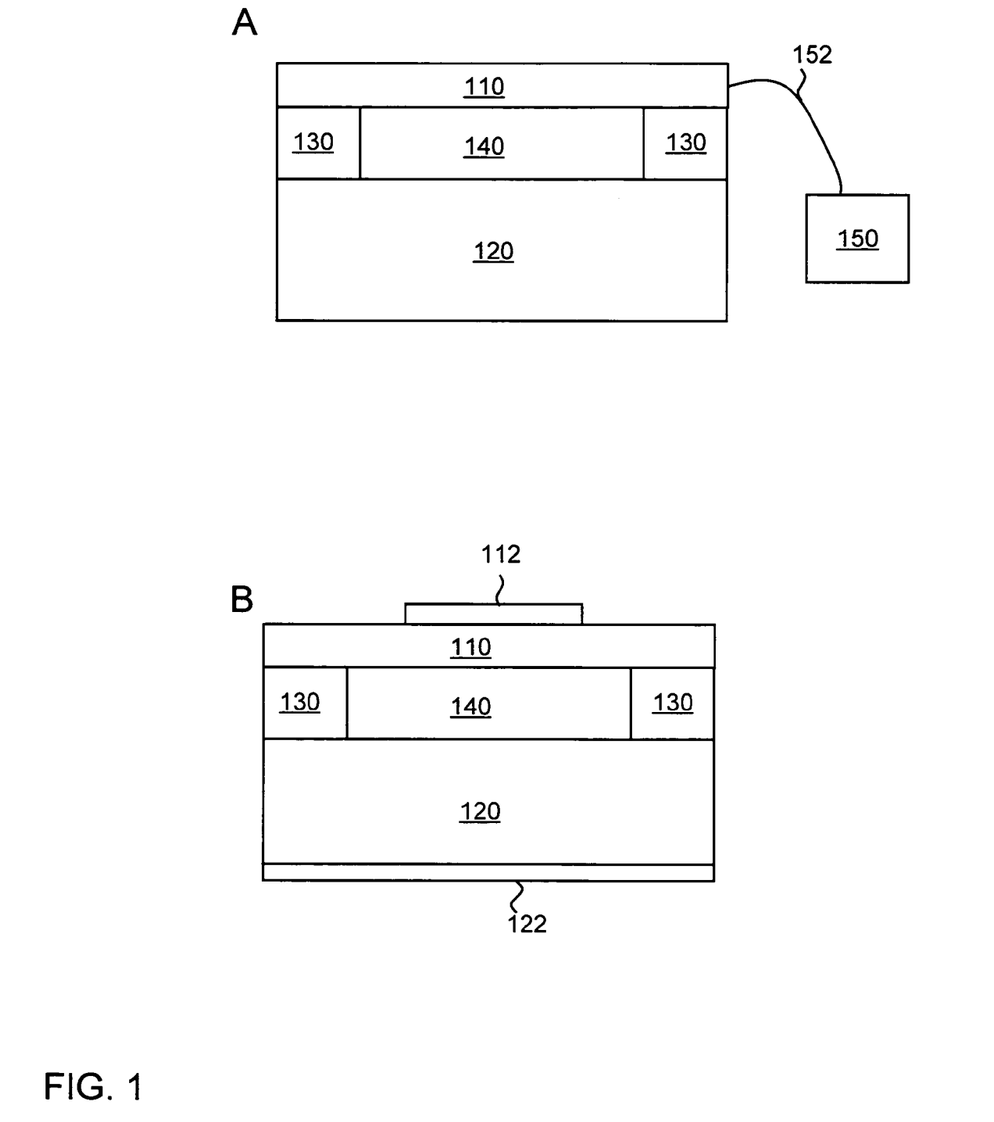
FIG. 1 shows cross-sectional diagrams of sensor elements according to the present invention.

The present invention provides a sensor comprising a plurality of sensor elements. FIG. 1 shows schematic cross-sectional diagrams of two examples of these sensor elements. The sensor element shown in FIG. 1A includes a functionalized membrane 110, which is supported over a substrate 120 by support frame 130. Functionalized membrane 110, support frame 130 and substrate 120 define a vacuum gap 140. Vacuum gap 140 is preferably between about 0.1 µm and about 5 µm in height. The sensor element is connected to a detector 150 through connector 152. Detector 150 may be any type of detector that can detect the mechanical resonance frequency of functionalized membrane 110. Examples include, but are not limited to an optical detector, a mechanical stress detector, a magnetic detector, and a capacitance detector.

In one embodiment of the invention, functionalized membrane 110 is driven thermally (by applied heat or by thermal noise) or electrically, and an optical detector is used to detect deflection or resonant frequency shifts of functionalized membrane 110. Interferometric optical detection techniques suitable for this embodiment are described in U.S. Pat. No. 6,567,572, by Degertekin et al., which is incorporated herein by reference. In other embodiments of the invention, functionalized membrane 110 may have thin piezoelectric or magnetic films that provide coupling. Resonant functionalized membranes 110 may be addressed by capacitor action (cMUTs), by a piezoelectric thin film (pMUTs), or by a magnetic film on the surface (mMUTs). Alternatively, the change in the membrane deformation may be measured directly through the change in capacitance, or magnetic field, or piezoelectric signal, or change in resistance through the piezoresistive effect, or optically using an interferometer, or any other detection modality to measure the change in the position of the membrane due to the attachment of agents to the film.

Preferably, functionalized membrane 110 operates at a mechanical resonance frequency of at least about 1 MHz, more preferably between about 1 MHz and about 100 MHz. Also preferably, the sensors have a Q factor of at least about 50.

Figure 2:
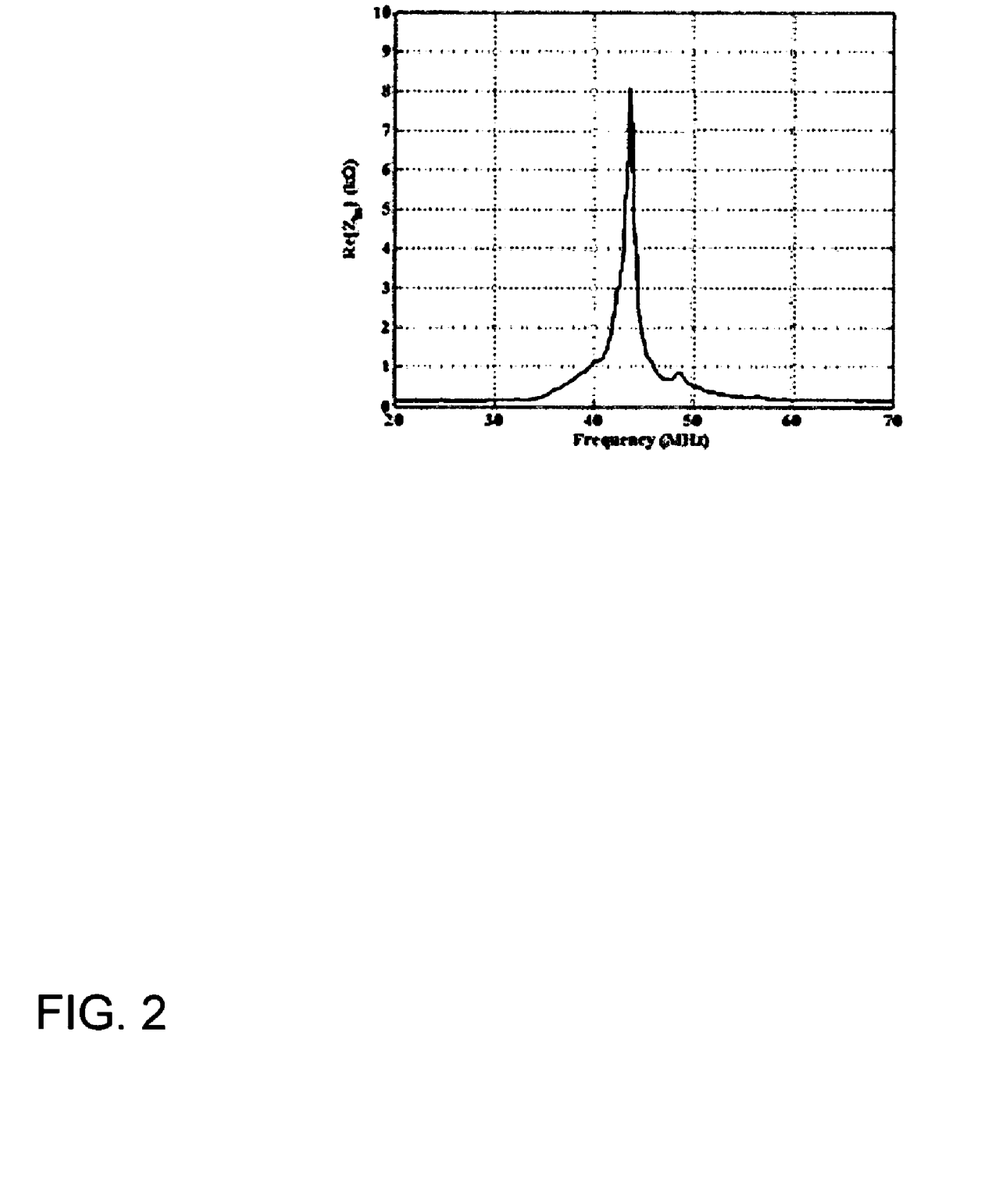
FIG. 2 shows an example of a resonance frequency response of a sensor element according to the present invention.

In a preferred embodiment, shown in FIG. 1B, functionalized membrane 110 contains a first electrode 112, and substrate 120 contains a second electrode 122. In this case, functionalized membrane 110 and substrate 120 are made of thin membranes that are essentially parallel plate capacitors with a gap between the plates. In a preferred aspect of this embodiment, the conductive silicon wafer on which the functionalized membrane is fabricated, i.e. substrate 120, makes up one plate of the capacitor; a metal electrode 112 on top of the functionalized membrane 110 is the other plate of the capacitor. Functionalized membrane 110, which is supported by insulating support frame 130, is typically made of an insulating material, most commonly silicon nitride ($Si_3N_4$) and is coated with metal electrode 112. A low temperature oxide passivation layer may cover electrode 112 and functionalized membrane 110. A typical resonant frequency response of this type of sensor element is shown in FIG. 2. In one embodiment, functionalized membrane 110 is constructed to have a large surface area, for instance by adding vertical trenches, or by making a portion of the membrane porous. In this fashion, it is possible to attach many more molecules of a species to the membrane and increase the mass loading or induced stress, and hence improve sensitivity.

Figure 3:
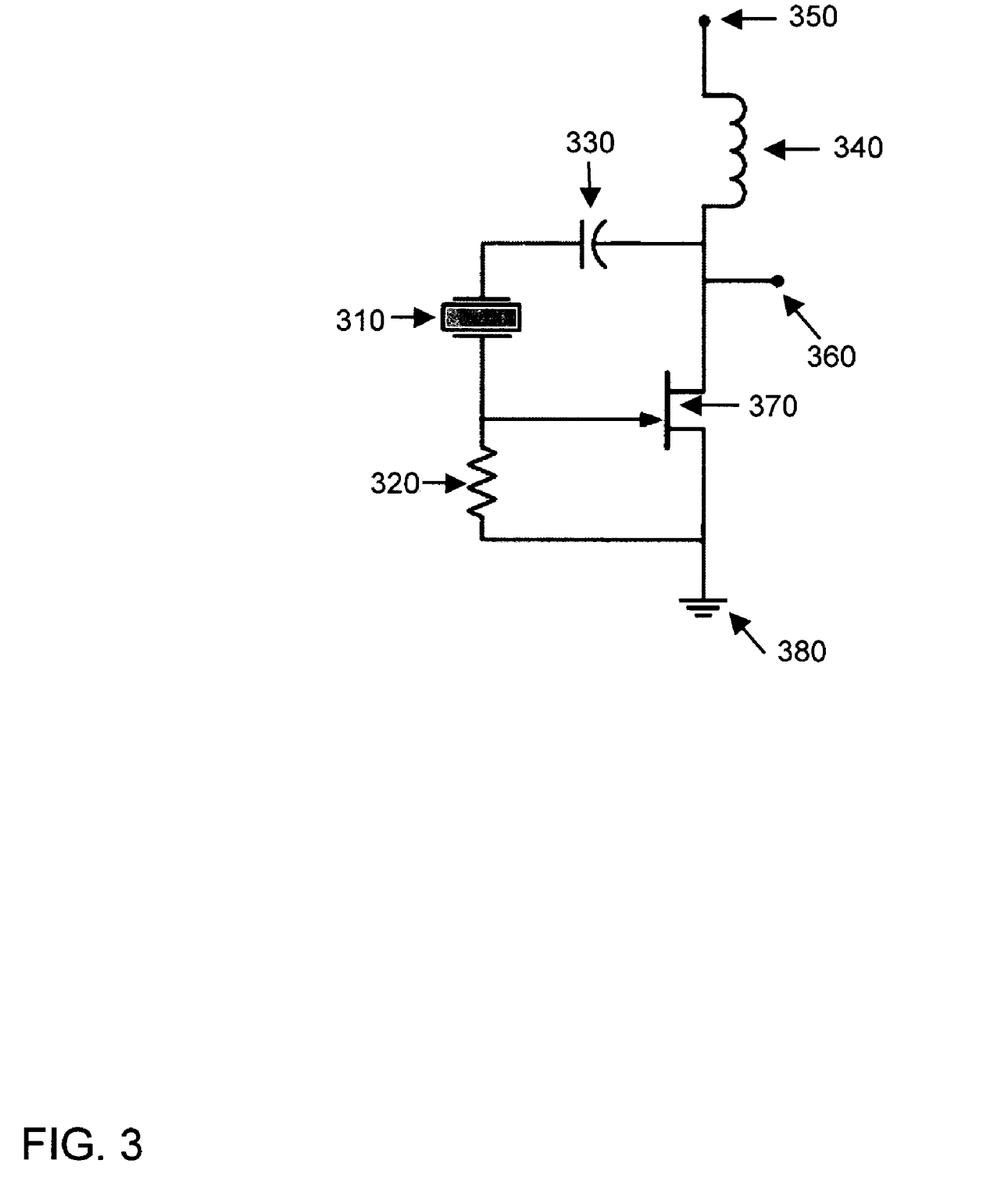
FIG. 3 shows an example of an electrical circuit for a sensor according to the present invention.

A typical circuit for using a sensor according to the present invention is the so-called Pierce oscillator, one variation of which is shown in FIG. 3. The circuit includes sensor element 310, resistor 320, capacitor 330, inductor 340, DC voltage source 350, sensor output 360, transistor 370, and connection to ground 380. Many other circuits are available to establish a resonant circuit using the sensor element's resonant electrical input impedance. The output of these circuits is a sinusoidal signal whose frequency is the measurable quantity of interest.

Generally speaking, the sensor element is placed in the feedback loop of an amplifier and the gain of the amplifier is adjusted such that the circuit oscillates. The frequency of the oscillator is tuned by adjusting the DC bias that is applied to the sensor element. By controlling this DC bias the resonance or oscillation frequency is placed near the open circuit resonant frequency of the sensor element. This is done in order to reduce the noise in the oscillator circuit, and hence increase the sensitivity of the sensor element. When something deposits on the membrane of the sensor element, its open circuit resonance frequency shifts, and this imparts a frequency shift in the oscillator circuit. By measuring the resonant frequency of the oscillator, one can tell how much mass has deposited on the membrane.

Figure 4:
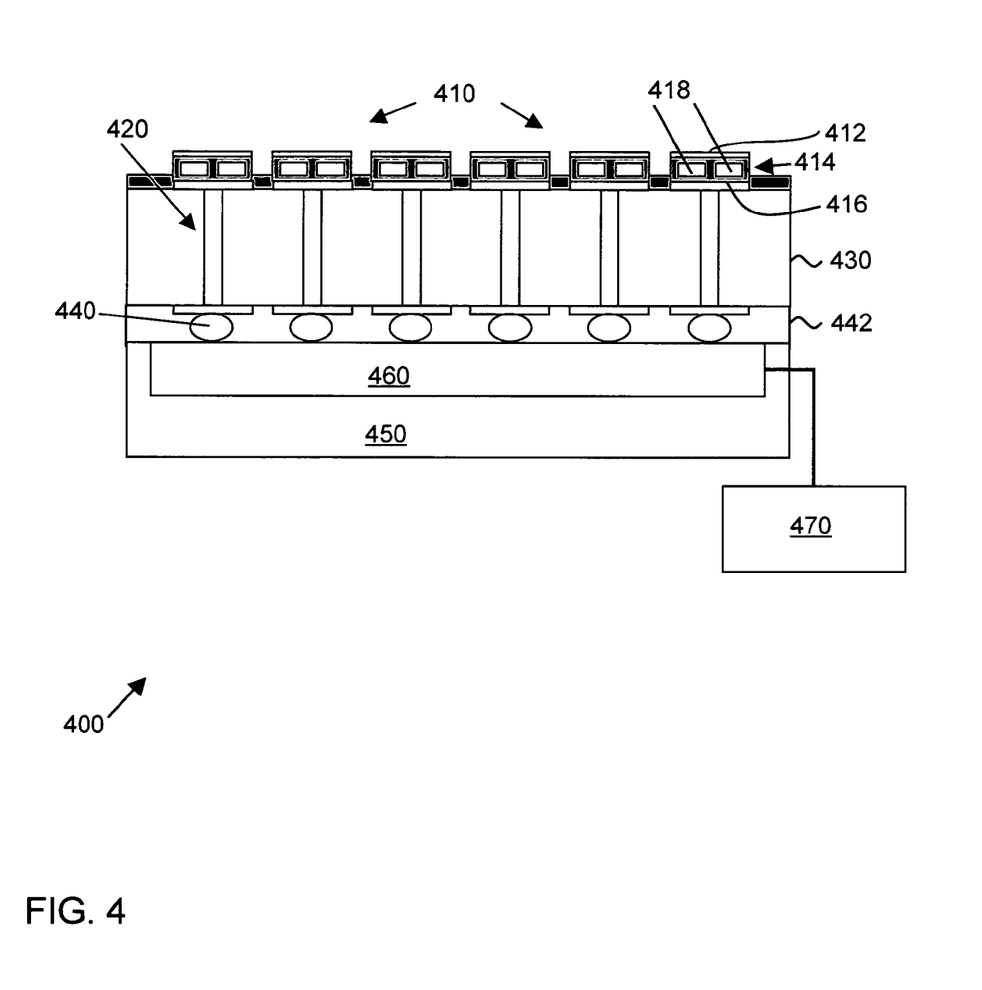
FIG. 4 shows a schematic cross-sectional view of an array of sensor elements according to the present invention.

FIG. 4 is a schematic cross-sectional view of a sensor device 400 containing an array of sensors 410 according to an embodiment of the invention. In this example, each sensor 410 contains two sensor elements, each of which has a sensor membrane 412, support frame 414, substrate 416 and vacuum gap 418. However, any number of sensor elements may be used for each sensor. Alternatively, one sensor with multiple sensor elements may be used. The exterior surface of each sensor membrane 412 is chemically functionalized to have an affinity for one or more specific, predetermined chemicals. The chemical functionalization can select for the presence of specific explosives or biohazard chemicals, but may also select for perfumes and other aromas, as well as other chemicals in commercial and industrial applications. The sensor elements are designed for sensitivity to mass loading and stress loading by the adhered chemicals, and for matching into the electronic circuitry such as a Pierce oscillator or any other type of oscillator that is used to detect the shift in the property of the membrane. Due to the chemical functionalization of the membrane surface, the specific predetermined chemicals attach to the surface of the membrane 412 when they are present in the environment. Consequently, the operational characteristics (e.g., capacitance or resonant frequency) of the sensor element will be altered.

The presence of the chemical in the environment can then be measured by detecting the alteration of the operating characteristics of the sensor element. For example, an alteration in sensor element characteristics can be detected by measuring the capacitance of the sensor element, or by measuring the change in the resonant frequency of the functionalized membrane. Interconnects 420 through wafer 430 provide electrical contacts from the sensors 410 to a wafer 450 with electronics layer 460. The interconnects 420 are separated from the electronics 460 by an underfill 442 and solder balls 440. (While solder bumps are shown in this figure, contacts may be made between wafer 430 and wafer 450 by any means known in the art, e.g. with an anisotropic conducting film). The electronics layer 460 contains appropriate circuitry to drive and detect operational characteristics of the sensors. Additional signal processing electronics 470 may be attached to the sensor electronics to further process the signals and provide an indication of the presence of specific agents. The signal processing electronics measure and track the frequency output signals from the sensors to indicate the presence of agents.

Figure 5:
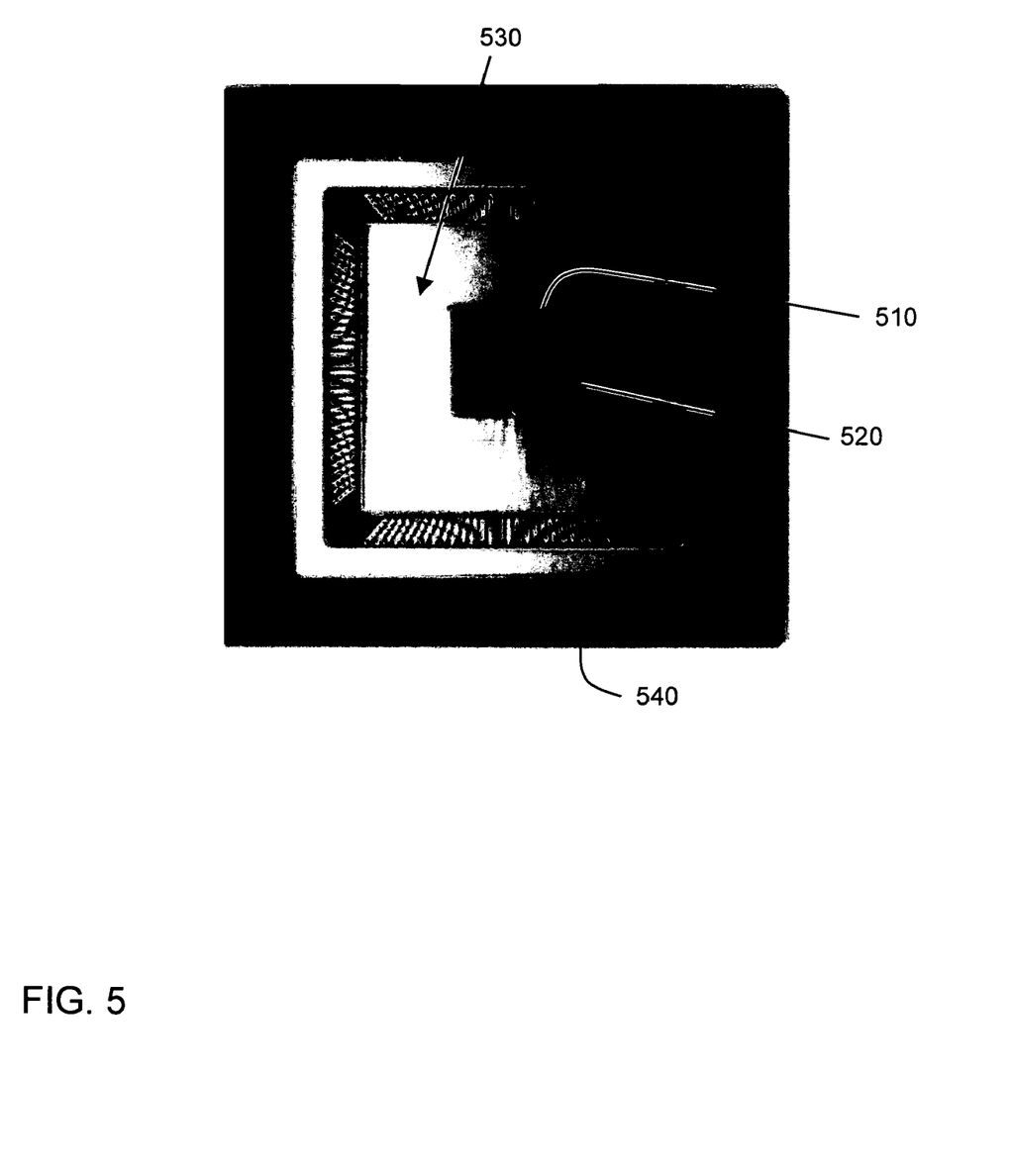
FIG. 5 is a photograph showing a top view of a 16×16 sensor element array according to the present invention integrated with electronics using solder bumps.

FIG. 5 shows an example of a sensor according to the present invention. In this example, a 16×16 array 510 of sensor elements (total=256, measuring 4 mm×4 mm) is bonded to a custom integrated circuit (IC) 520 for driving and detecting operational characteristics of the sensor. The custom IC provides a resonator circuit below each sensor element and multiplexers to provide the outputs of these resonators to an external frequency counter and a digital computer for data collection, processing, and storage (not shown). Gold wires 530 are used to bring out the contacts from the IC to a package 540.

Figure 6:
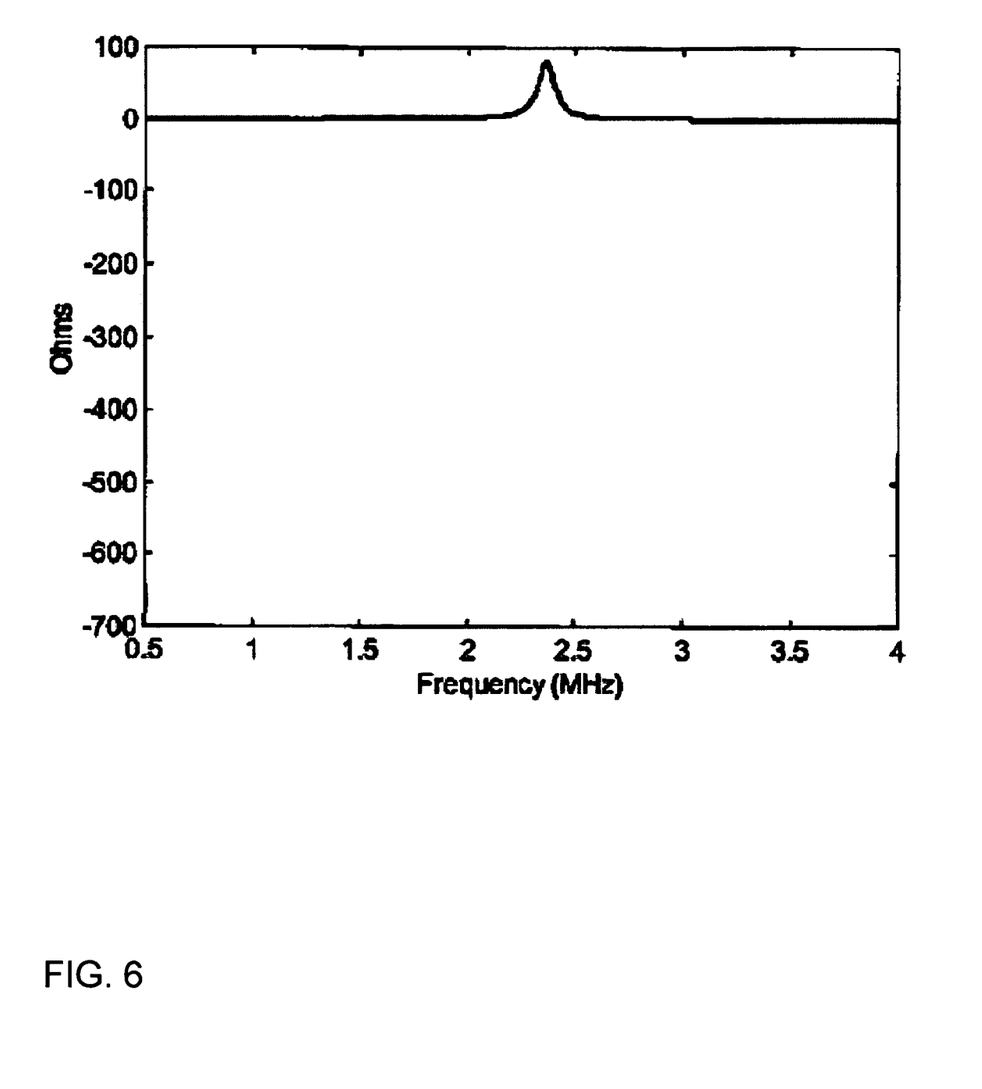
FIG. 6 shows a typical input resistance of a sensor element according to the present invention.

The material properties and dimensions of the functionalized membranes determine the resonant frequency of the sensor element. In order to create a high electromechanical coupling coefficient, a DC bias is applied to the functionalized membrane to maintain a very high electric field in the vacuum gap. For instance, a silicon nitride membrane 12 μm in diameter and 0.4 μm thick will resonate at a frequency of 42 MHz. The typical input resistance (i.e., real part of input impedance) of such a device, made of 110 sensor elements each 12 μm in diameter, is shown in FIG. 6. Each sensor element is used as the resonant tank of an oscillator circuit, where the resonant frequency shift indicates the amount of mass loading on the membrane. The sensitivity of such a resonator is defined as the ratio of the frequency shift over the frequency: $\Delta f/f = -\Delta m/2\,m$, where $\Delta m$ is the change in mass (i.e., mass of the species that adhere to the sensor) over the total mass of the membrane. Operating in the 50 MHz range, this sensor would have a sensitivity that is orders of magnitude greater than the sensitivity of a cantilever in the 50 kHz frequency range.

In one embodiment, the resonant frequency response of the fundamental mode is supplemented by also measuring a series of higher harmonics of the membrane. The viscoelastic properties of the sensing layer (e.g., polymer) are influenced by absorption/adsorption. These properties are extracted through measuring the frequency dependence of the damping and the amplitude of higher order modes, and these measurements provide chemical information in addition to the resonant frequency of the structure. For instance, different mass loadings, polymer swelling and changes in the young modulus are detected through the amplitude $A_n$ and Q-factor $Q_n$ of the modes n=1, 2, 3, 4, etc. Off-resonance response may also provide information on viscoelasticity through the slope of the mechanical response. In some instances, the membrane in a sensor element can be engineered to enhance the response at some harmonics.

In another embodiment, sensitivity is increased by integrating and collecting molecules in the sensing layer. Here gas or liquids are exposed over a layer that binds the molecules of interest fairly strongly such that they are integrated in the sensing layer. The temperature of exposure will depend on the chemical desorption rate, and may be at room temperature or at lower temperatures depending on the molecule. After a set time, the sensor elements may be heated either by thermal pulse or a linear programmed temperature ramp. During this heating, the molecules will be desorbed and the change in resonant frequency and Q-factor will show a particular desorption profile similar to thermal desorption analysis commonly using man spectrometric systems or gravimetrically (thermogravimetry). The temperature of desorption is an additional parameter that is sensitive to the chemical nature of the absorbent-absorbate interaction. After one thermal desorption cycle, a second subsequent cycle may be used to provide a reference calibration to be subtracted as a baseline from the first. The second thermal cycle will reflect the thermomechanically induced change in resonance frequency.

The use of electrodes in arrays of sensor elements provides a convenient method to heat the individual elements of the array. The small size and structure of the sensor elements ensures that low energy consumption, low thermal loads and fast (sub millisecond) response times can be achieved. The latter is very important for good resolution in the desorption profile. Note the temperature readout of the units is also possible through a) integration of small thermocouples and b) the resistance of piezoresistive layers and other means. The actual temperature profile during heating can provide information on phase transitions, heating or cooling effects. The sensor structure, being a bimorph element, may be readily optimized to create an array of thermal sensor elements working on the bimetallic effect. Here temperature changes induce both changes in resonant frequency and static bending. As with previous cantilever experiments, different forms of calorimetric analysis such as differential scanning calorimetry (DSC) can be performed to provide additional data to identify substances. The use of catalytic layers also enables the identification of a chemical or biochemical by heat produced by chemical reactions, e.g., $CO + O = CO_2$ (catalyzed by platinum).

In another embodiment, sensors make use of a response to ir-uv illumination. Specific chemicals exhibit absorption bands resulting in electronic and/or vibrational excitation. All of these absorptions result in a thermal loading of the structure/sensing layer. Changes in materials such as a metalopthalocyanines or the presence of the chemicals therefore change stress, frequency and static deflection. Scanning of the incident length of a chopped beam or the response of a series of lasers or LED's at different frequencies may be used with the arrays to specifically detect analytes in liquid, gas or vacuum.

In sensors used in liquid environments or in a solid state electrode environment, the application of electrochemical potentials may be used to create fast cyclograms of liquid, enabling detection of chemicals through their electrochemistry. This is applicable also to biochemical detection.

Sensors may contain a single sensor element, one-dimensional arrays of sensor elements, or two-dimensional arrays of sensor elements. In one embodiment of the invention, a sensor is formed from one sensor element. It can be used as a sensor on its own, in the same fashion a cantilever is used as a sensor on its own. Alternatively, multiple sensor elements can be used in parallel to form one sensor so that the signals from the sensor elements may be sensed coherently. Coherent sensing from multiple sensor elements has many advantages including reducing the probability of false alarms.

Multiple sensors can in turn be combined to form one-dimensional arrays or two-dimensional arrays of sensors. An advantage of a two-dimensional array is that an entire wafer may be populated with thousands of sensors, each containing multiple sensor elements. A one-dimensional array provides surface space, which may be used to integrate electronics side-by-side with the sensor elements. In a preferred embodiment, a two-dimensional sensor array has electronics flip-chip bonded or fabricated under the sensor array.

Having a sensor device with thousands of sensor elements to make one sensor is very useful in establishing the electrical impedance of the sensor, and probably more importantly in reducing the number of false alarms as all the membranes or cells in a sensor operate in parallel, and if one were to give a false indication, all the other ones force a correct decision. Having thousands of sensors or sensor elements, many of which are functionalized in the same fashion, can also be used to reduce the false alarm rates and provide a much more correct and stable measurement of the presence of an agent.

It should be emphasized that sensors containing multiple sensor elements may have elements whose membranes have different resonant frequencies. A membrane operating at low frequency yields a sensor more sensitive to stress on the membrane, whereas a membrane operating at high frequency gives a sensor that is more sensitive to mass loading. Combining various operating frequencies in one sensor thus provides a sensor with a greater versatility.

In such embodiments, electronics are preferably integrated with sensors, where multiple elements are attached in parallel, and sensors are operated at different frequencies so that one output line could be used. For this purpose, different sensor elements are built and operated at different frequencies. For example, a row of sensor elements can be made to resonate from 45 MHz to 55 MHz in 0.1 MHz intervals. Principles of dense wavelength division multiplexing (DWDM) may be used in such devices. A sensor for a Dog Nose type sensor may be made of one of multiple capacitor membranes that are all attached in parallel by virtue of having a metal electrode that covers all the sensor elements partially or fully. By altering the diameter of sensor elements, it is possible to change the frequency of operation of a resonator made with a sensor element. Having sensors operating at multiple frequencies can have advantages in electronic integration in transmitting information at different frequencies on the same channel, and in separating the influence of stress and mass loading on the shift in resonant frequency of a resonator.

In one embodiment, sensors also include reference elements. The reference elements include an unfunctionalized membrane instead of a functionalized membrane in the sensor element. The number of elements that will be used as reference may be easily determined experimentally. Typically, it is expected that 1% to 50% of the sensors will be left without a function and used as a reference. Also, thermistors may be imbedded in the array of sensors to provide temperature measurement for temperature compensation. Also, a non-functionalized sensor and a functionalized sensor may be used as a differential pair where their resonant frequencies would be designed to be the same and the difference would then subtract out temperature effects.

In one embodiment, large arrays of sensors or one sensor with an array of sensor elements may be used to develop a physics/chemistry based model to extract unique inversion for single element identification using multiple functional agents. In particular, collecting data about the sensitivity to certain species by different functionalizing chemistries allows the development of a model to relate the outputs of the multiple sensors or sensor elements to the different species with higher accuracy. Such models are standard for instance in IC manufacturing where pieces of equipment have multiple input or control variables such as temperature, pressure, flow rate, etc., and where the result of a process is either film thickness or stoichiometery or any such variable. Physics-based or data-based experimental models are constructed to relate the outputs to the inputs and thus provide better recipes for providing the desired output product. The same can be used in the multi-sensor (or sensor element) case where various finctionalizations are realized to identically identify certain species with excellent sensitivity.

One of the major advantages of arrays of sensors according to the present invention is the ability to make thousands of sensor elements side by side on the same wafer. All these may be integrated by chip-to-chip bonding to wafers that contain all the electronics needed to set up the sensors as resonators and to provide an output that can be analyzed in an electronics box to calculate an output, which would be the species detected and its amount. The large number of arrays is provided to make more accurate measurement through a model based detection, through multiple measurements to remove and reduce false indications.

In one embodiment, arrays of sensor elements are functionalized by a wide range of sensor materials. For example, for polymer sensors some 500 polymers with a redundancy factor of 10 may be used. The specific responses including orthogonality of response, operation mode (temperature, integration times, etc.), lifetime and sensitivity of environment or other disruptory influences may be tested using the target molecules and interfering agents. Based on a self-optimization the system may then select the most sensitive polymer basis set (say 10 polymers) and optimum mode of operation. In this way, different customers, corporate (food, perfume), medical (breath, urine, blood analysis), security or military can obtain rapidly prototyped solutions. Incorporation of this data in a database for future development of prototypes and known response functions can be used.

A key feature of sensor element arrays according to various embodiments of the invention is that the vast number of independently addressed sensor elements in the array allow for a massive redundancy. For instance, in an array of 5000 sensors elements, one can have a redundancy factor of 100 using 50 sensing and reference materials. This ensures that false alarms or defective elements in the arrays which might miss the detection of chemicals are not an issue in device operation. The self calibration and learning feature of such arrays is also a mode which takes full advantage of redundancy. It permits defective elements and the control quarantine and analytical potential of the device to be optimized on the fly. Furthermore, it permits new threatening chemicals that may be identified as a signature of terrorist activity to be immediately introduced into the detection capabilities of machines installed at different operational locations.

During extended operation in different environments, differences in humidity, air composition, pollution, temperature, etc., may cause temporal shifts in a gas sensor array which will be reflected in the overall frequencies, Q-factors, desorption profiles, etc., of the sensor elements. In order to maintain constant calibration, the devices may be periodically (e.g., once per hour) exposed to a series of tiny ppb quantities of trace gases that are being searched for, for example, small quantities of dinitro-toluene (DNT). This exposure provides a model response of the system diluted in ambient gas that the sensor array is seeking. Neural network/fuzzy logic learning cycles are used to program the devices selectivity. Likewise, possible false alarm chemicals such as deodorants and humidity shifts may also be introduced to further calibrate the system. New potentially hazardous chemicals can also be introduced into a self-calibration bank of chemicals. The calibration bank is made of dilute samples in pencil sized containers whose introduction into the system is controlled by a programmed gas handling system.

Multiple independent sensor element arrays in their own separate head-space or sniffer systems may be used. In this way an array can be taught while others sample. If a suspicious chemical signature is detected before an alarm is sounded (red) an orange status response can be initiated. Here the reference compound can be injected into the sensor array(s) that detected the suspicious signal enabling comparison to clearly identify and initiate a red response.

Sensors according to the present invention may be used with swabs and vacuum samples with swabs. The sensors may also be integrated into current devices and used as a means of comparison or optimization. Head space analysis using small sensors also enables much smaller samples to be used because the head space volumes can be reduced. Thermal control of head space analysis is also faster because of the small dimensions of the space volume.

Arrays of cMUTs have been produced to fill an entire 4-inch silicon wafer (Oralkan et al., IEEE Trans. on UFFC 49, no. 11, 1596-610 (November 2002)). Each element was 420 μm by 420 μm in size, contained 72 capacitor cells, and had a through wafer interconnect to carry electrical contact from the back side of the wafer to the cMUT. Recently, these cMUTs have been bonded to integrated circuit electronic dies for medical ultrasound imaging applications. A similar configuration may be used in accordance with embodiments of the present invention for resonators with functional chemical layers on their surfaces.

Sensor elements according to the present invention may be made with any of various known CMUT fabrication techniques including: SOI bonding, sacrificial layer, surface or bulk micromachining, and silicon on insulator bonding. The metal on the membrane is chosen to ensure the adhesion of the functionalizing chemical. The sensor element itself is designed for maximum sensitivity while taking into consideration its mechanical loading and electrical interfacing into the integrated (or non-integrated) electronic circuitry. Sensor elements of the present invention may be integrated with electronics in any of various known configurations including: flip chip bonding, elements constructed on top of electronics, or vice versa. The sensor elements may be fabricated with through wafer vias or trench isolated by etching through the back side using various well-known techniques for cMUT fabrication. Techniques suitable for fabricating such sensors are known in the art and are described, for example, in B. T. Khuri-Yakub and L. Levin, U.S. Pat. No. 5,828,394, which is incorporated herein by reference.

In preferred embodiments, a CMOS provides the circuitry to read out the loading of the membrane either through a capacitance shift by direct measurement, resonant frequency measurement, or any of various other means. The outputs of various sensors can be multiplexed, then the frequencies can be measured by a frequency counter and these outputs can then be digitized and stored and processed in a digital computer. The computer then can display the variation of the resonant frequency versus time and provide results of analysis of sensed species based, for example, on previously loaded models of sensitivity of multiple sensors to various chemicals.

Some processing of information can be done near the sensor. For instance, time averaging or multiplexing or digitization can be all processed in the vicinity of the sensor before being transmitted to a computer or a circuit board with a multiprocessor. Specific algorithms can be loaded in memory to perform the same functions one would in a digital computer and then drive displays where colored outputs can be used to indicate level of detection or hazard.

As in many sensors deployed today, such as RF tags and implanted medical devices, it is possible to use RF antennas to couple and provide power to the sensor. Once a sensor is powered, it senses its function, then the output of the sensor is re-radiated to a receiving antenna. In this fashion, the sensor can be passive and remotely addressed.

Sensors according to the present invention may be functionalized in various ways including the use of ink jet techniques, spotter techniques, microfluidics, self-assembly, shadow masking coupled with the above, or spraying in vacuum through movable mask arrays, to name just a few. In some embodiments, an array of sensor elements is functionalized with polymers having different properties so that the sensor array can sensitively detect and differentiate chemical compounds, and even complex mixtures such as flavors and fragrances. The polymers used may be similar to those used by Baller et al. [Ultramicroscopy 2000, 82, 1-9] and Battiston et al. [Sensors and Actuators B-Chemical 2001, 77, 122-131] in cantilever devices. Generally, one may select and test an optimum set of polymers to generate a robust signature for a compound such as explosives vapors. Polymer elements respond to gas-phase analytes in seconds to tens of minutes. The selection of polymers is preferably optimized to best fit the mechanical properties of the sensor element (elasticity, density, etc.), so that detection time is minimized and sensitivity is maximized. The sensor element surface is functionalized to improve the polymer film's stability, control analyte adsorption kinetics, and ease polymer application.

In some embodiments, neutral polymer gels may be used as carriers for chemical compounds such as explosive-analyte binding compounds. Using this method, a variety of compounds that do not form stable films themselves can be applied through drop or spin coating on a neutral substrate such as silicon dioxide. For example, Yang et al. used a 15-30 nm film of polymethylhydrosiloxane (PHMS) carrying functionalized cyclodextrins to detect vapors of o-nitrotoluene, DNT, and trinitrotoluene (TNT) with ppb sensitivity.

Chemical functionalization may be performed, for example, by first coating the exterior surface of the sensor membrane with a metal such as gold that insures adhesion of a functionalizing chemical to the surface. The chemical itself may be deposited on the surface using various techniques such as drop ejection that enable multiple functionalizing liquids to be deposited on the sensor surface, and also ensure that there is no cross-contamination between adjacent functionalized cells of an array. In order to control the location, applications, volume, and quantity of liquids deposited on the surface, one may use ink jet technology with functionalizing chemicals instead of inks. It is also preferable to use non-thermal deposition technology as thermal ink jets can harm sensitive fluids. A drop ejector, for example, may be used to deposit the polymer over a sensor. The drop ejector is used to deposit enough drops to cover a sensor. Different ejectors are used for different chemicals so that adjacent sensors and sensor elements can be functionalized differently. A preferred deposition technique is to use ultrasound based ejectors where a focused beam will evolve a drop from a free surface. Using this technology it is possible to eject drops as small as 3 microns in size with a velocity of a few meters per second, on demand, and with energy of the order of nano-Joule.

In other embodiments, various other types of sensing materials may be doped or functionalized as required. These materials include, for example, polymers (co-polymers, biopolymers), sol gels, porous materials (silicon, zeolite, etc.). DNA, RNA, proteins, cells, bacteria, carbon nanotube arrays, catalysts including metals to enzymes, nanoclusters, organic and inorganic materials including: supramolecules, metal-organic complexes, dendritic materials.

Sensors according to the present invention may be used in liquid, gas, or vacuum. Operational temperatures range from cryogenic to high temperatures, depending on the limits of the sensor materials. For operation in immersion, the cells in the cMUT or pMUT or mMUT, or whatever variation, could be made with cells that are distant from nearest neighbors, by design, to provide a narrow band operation. Thus, the devices in immersion would have narrow bandwidth, allowing resonators with low noise. This is a design criterion that is contrary to cMUT design for medical imaging which call for very broad band operation.

Sensors according to the present invention can be used in various ways. In one embodiment, sensors according to the present invention may be connected down stream from a separation system (such as used in chromatography or gel electrophoresis) to detect specific signatures in complex mixtures of liquids. In this embodiment, relatively simple baffle structures created on chip may provide a further analytical signal input for the device to learn chemicals through processing of the relative time delays caused by different diffusion properties of chemicals sensed between individual sensor elements on one chip or between a plurality of chips. The principles of such devices may use the human nose as a model, which has a duplicity of sensors where the time delays are used in the smelling process.

In operation, a sensor according to the present invention can be mounted on a wall, ceiling or other portion of a fixed structure, incorporated into a hand-held device, or mounted on a moving vehicle, to name just a few examples. Depending on the specific application, it may be used with or without active circulation of chemical-containing gas or liquid fluid over the sensors to increase exposure of the sensor to chemicals in the environment. A general requirement for high sensitivity in detection of small quantities of chemical biohazardous materials is to integrate the sensor as close to the sampling inlet as possible. The small dimensions of the arrays readily facilitate the integration of the sensor at even millimeter distances from the sampling inlet. Furthermore, they provide the possibility to integrate a plurality of independent sensor units in a small space, which is essential in some applications. For instance, ring arrays may be made with sensor elements that are 30 microns in diameter and where nine sensor elements are connected together to form a sensor, thus making a sensor that 100 microns by 100 microns in size. Single sensor elements with a diameter of 10 microns may be constructed and used in 1D array elements. Resonant devices may be made with sub-100 micron dimensions.

In some embodiments, two sensor units may be used in a Dog Mode. One unit samples gas from ambient, the other unit samples gas closer to the suspicious object. First, both sensors sample the same ambient and cross calibrate responses. The second phase in which they perform differential sensing looks for essential differences in response. This is similar to a dog, which moves its head sideways to and fro sensing differences in chemical gradients.

The Dog Mode using more than one sensor can also be used to physically track scents of people or chemicals in a diverse range of environments or locations. This includes the use of bomb seeking robots, handheld tracking devices by security, military and police. The sensors may be incorporated on unmanned aircraft vehicles (UAVs) to assist in target identification, navigation, and information gathering. The guidance systems input may be controlled by the spatial variations in chemical gradients through a series of sampling apertures which also may operate in a wagging mode. Note the close proximity of the sensor to the inlet is achievable because of the small size of the device.

In liquids, the device can be incorporated into submarines, ships, divers' handheld devices or parts. Likewise, drinking water, toilets and anywhere liquids are used can be readily monitored or tracked. In another mode of operation, embodiments of the invention may be used as part of microfluidic devices enabling the detection of small (μL) micro liter volumes. The use of artificial Q enhancements can be applied to increase the sensitivity of the apparatus. Sensors of the present invention may be integrated with other devices and systems such as, for example, gas handling systems, self-calibrating systems.

Sensors of the present invention may be operated in Bloodhound Mode in which a sample of clothing or material peculiar to an object or person is provided to the system, which then programs the target response profile of the sensor array. Once programmed the sensor array will then be used to track out the target as described in Dog Mode.

Self calibration is also possible if the sample is introduced into a separate reference bottle. Samples as small as a grain of sand sized piece can be used because of the detector dimensions.

EXAMPLES

Sensor Results

Figure 7:
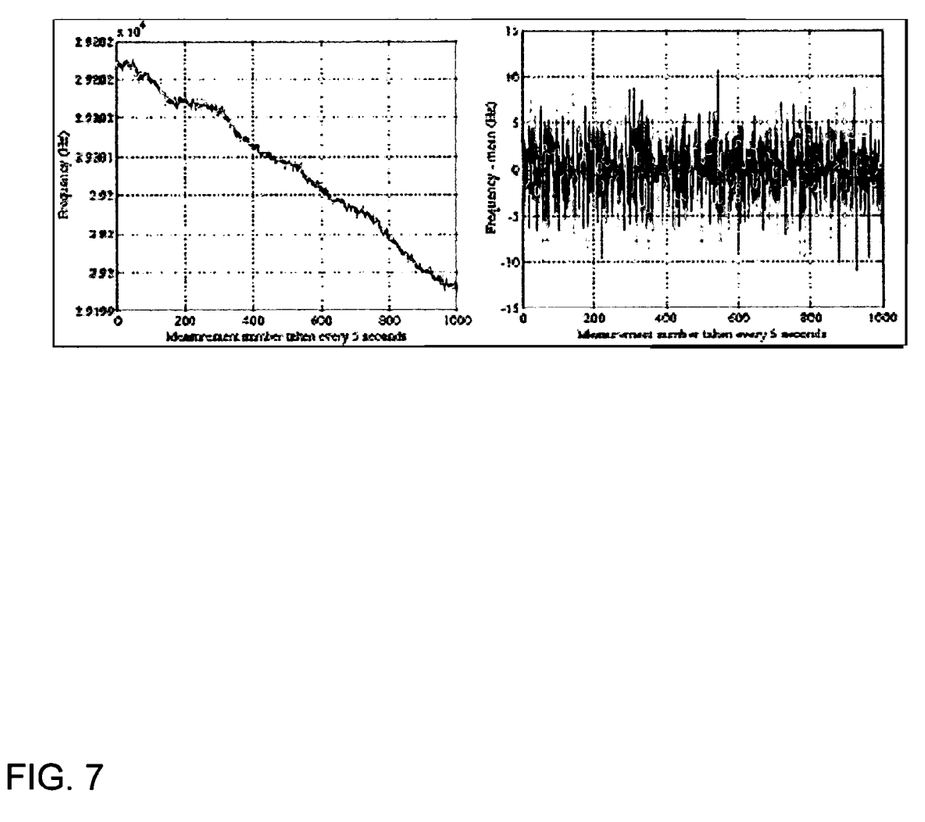
FIG. 7 shows the resonant frequency and average noise of a sensor according to the present invention.

A proof of principle experiment was done to demonstrate that a cMUT can be used in an oscillator circuit, and to demonstrate the ability to detect mass loading of a few species of interest. A 7 mm by 7 mm cMUT with over a thousand cells was set up in a Pierce oscillator circuit configuration, and resonated at 2.9 MHz. The resonant frequency and average noise are shown in FIG. 7 for 1000 measurements, each taken every 5 seconds. The measurement of FIG. 7 was done in a dry laboratory where temperature fluctuations result in frequency drift, which would be easily corrected with a reference oscillator as in the sensors described above. It is important to note that the noise floor ranges between +5 Hz and −5 Hz with a standard deviation of less than 1 Hz.

Figure 8:
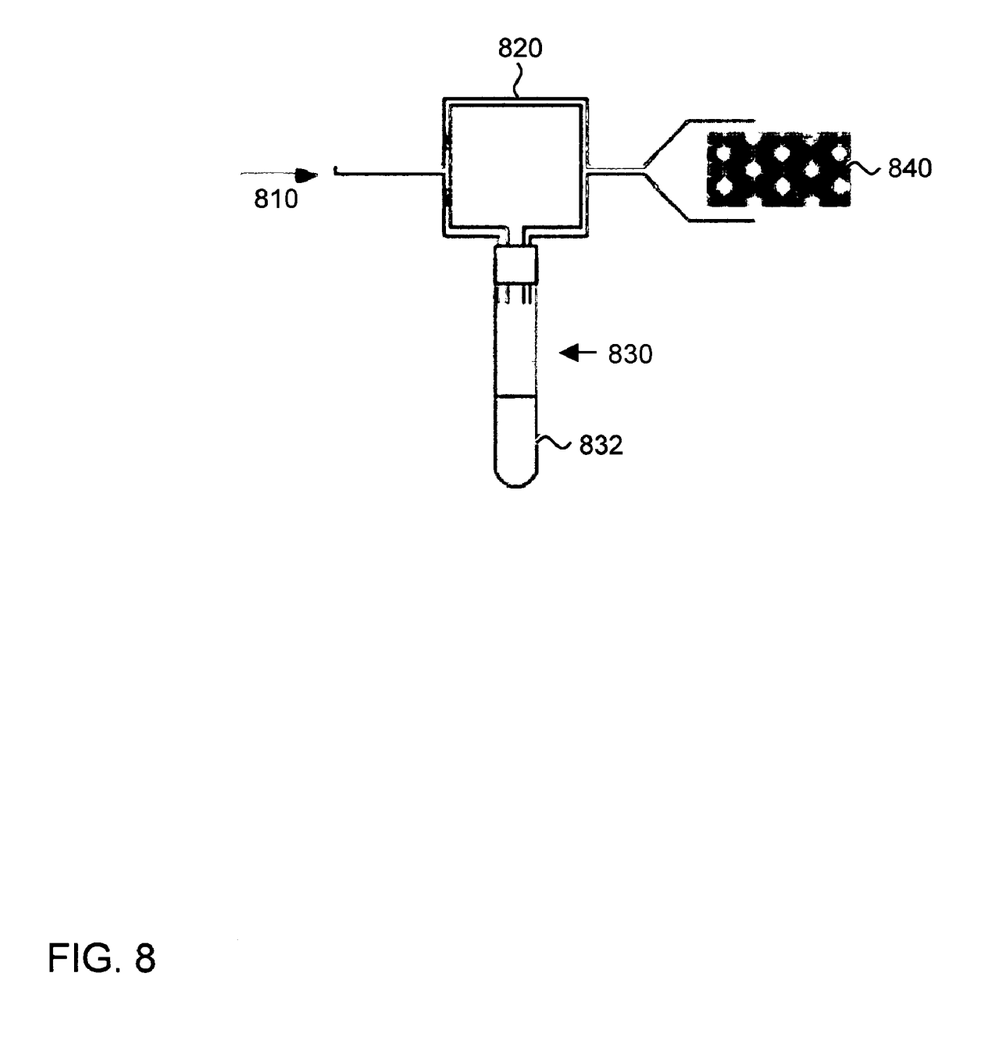
FIG. 8 shows an experimental set-up for detecting molecules carried by nitrogen gas over a sensor according to the present invention.
Figure 9:
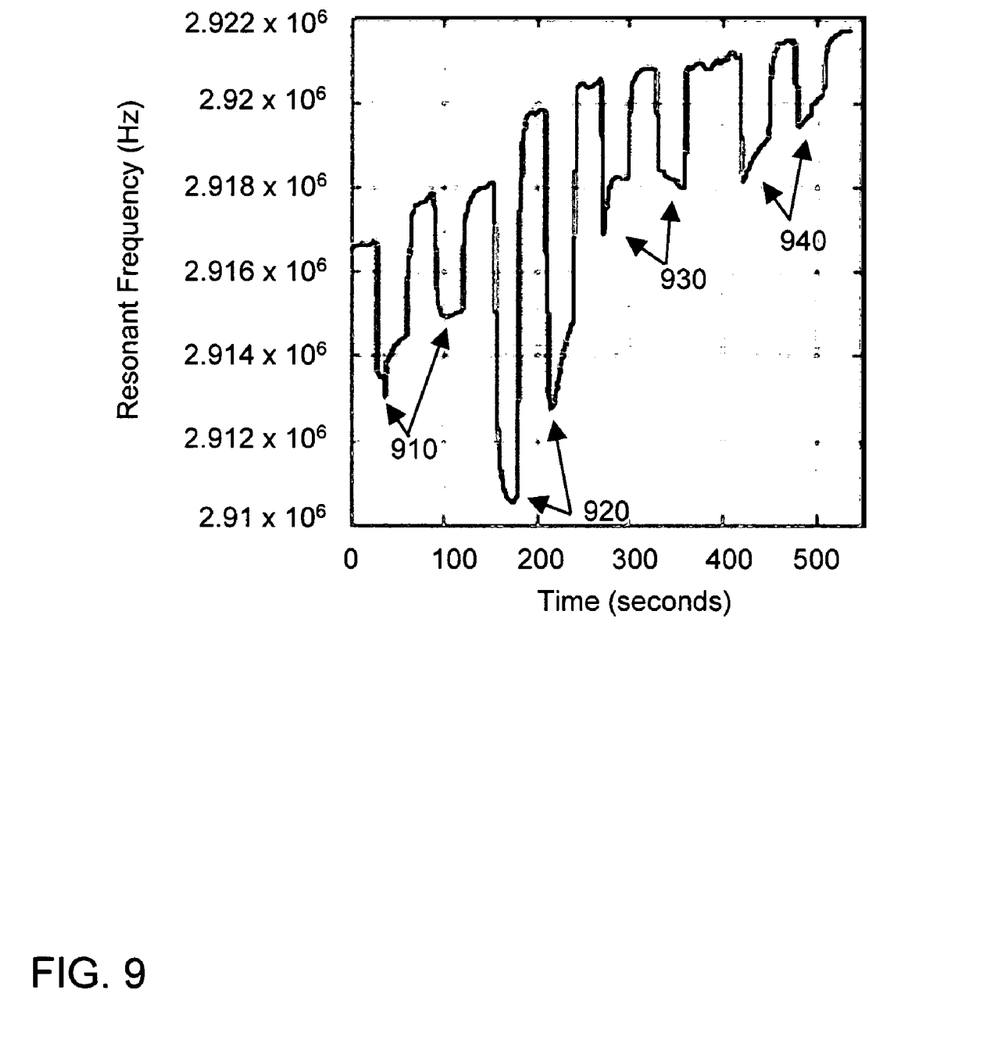
FIG. 9 shows frequency shift of a sensor according to the present invention due to mass loading by molecules using the experimental set-up of FIG. 8.

To test the mass sensitivity of the cMUT resonator the experimental set-up of FIG. 8 was used to detect the passage of four different species: water, Isoproposanol, Toluene, Di-Nitro-Toluene. The experimental set-up contains a nitrogen intake arm 810, a reference arm 820, and a test tube 830 containing liquid or crystal agent 832. The set-up outputs to a cMUT resonator 840. The protocol used to demonstrate the ability of the cMUT resonator to detect mass loading comprised passing nitrogen gas through the reference arm for 30 seconds, then switching the flow of nitrogen for 30 seconds into the test-tube containing the agent of interest. The process was repeated after the agent is changed while the nitrogen is flowing in the reference arm. The results of this experiment are summarized in FIG. 9. Arrows 910 indicate frequency shifts due to pulses of water, arrows 920 indicate frequency shifts due to pulses of isoproposanol, arrows 930 indicate frequency shifts due to pulses of toluene, and arrows 940 indicate frequency shifts due to pulses of Di-Nitro-Toluene. These results demonstrate that a cMUT based oscillator is a very sensitive mass loading detector.

Sensor Designs

Two important metrics in the performance of the cMUT sensor are the sensitivity to mass loading and the minimum detectable frequency shift of the oscillator. Two designs with silicon nitride membranes were considered for this evaluation. The parameters of the two designs are shown in Table I.

TABLE 1

|  | Design 1 | Design 2 |
| --- | --- | --- |
| Membrane Radius (μm) | 15 | 10 |
| Membrane Thickness (μm) | 0.8 | 0.356 |
| Gap (μm) | 0.1 | 0.1 |
| Electrode Radius (μm) | 7.5 | 5 |
| Collapse (V) | 131.83 | 48.80 |
| Mem. mech. Reson. (MHz) | 17.111 | 17.111 |
| Number of membranes | 500 | 500 |
| $r_{LOSS}$ | $2.6\,e^{-7}$ | $2.6\,e^{-7}$ |

Based on results using an equivalent circuit model of the sensor, the sensitivity of design 1 at 100 volts is about $1.7 \times 10^{-17}$ gram/Hz, while design 2 has a sensitivity of $3.33 \times 10^{-18}$ gram/Hz at a DC bias of 30 V. The apparent better sensitivity of design 2 is because the membrane is thinner by a factor of 2.25, and the area of the device is smaller by a factor of 2.25. Assuming the 10 Hz minimum detectable frequency as in FIG. 7, designs 1 and 2 yield a minimum detectable mass of $1.7 \times 10^{-16}$ gram and $3.33 \times 10^{-17}$ gram respectively.

As one of ordinary skill in the art will appreciate, various changes, substitutions, and alterations could be made or otherwise implemented without departing from the principles of the present invention. Accordingly, the scope of the invention should be determined by the following claims and their legal equivalents.

What is claimed is:

1. A sensor comprising a plurality of sensor elements, wherein each of said sensor elements includes:

a) a functionalized membrane including a first electrode;

b) a substrate including a second electrode, wherein said first and second electrodes define a capacitor;

c) a support frame, wherein said support frame, said functionalized membrane, and said substrate define a vacuum gap; and d) an electrical circuit including said capacitor, wherein said electrical circuit provides a sensor output responsive to a mechanical resonance frequency of said sensor element, wherein said mechanical resonance frequency of said sensor element is responsive to binding of an agent to said functionalized membrane; and wherein said electrical circuit is configured to operate said sensor element at or near an open circuit resonance condition.

2. The sensor as set forth in claim 1, wherein said sensor operates at a frequency greater than about 1 MHz.

3. The sensor as set forth in claim 1, wherein said sensor operates at a frequency between about 1 MHz and about 100 MHz.

4. The sensor as set forth in claim 1, wherein said sensor is configured to operate in a gaseous environment.

5. The sensor as set forth in claim 1, wherein said sensor is configured to operate in a fluid environment.

6. The sensor as set forth in claim 1, wherein said functionalized membrane comprises silicon.

7. The sensor as set forth in claim 1, wherein said vacuum gap is between about 0.1 μm and about 5 μm in height.

8. The sensor as set forth in claim 1, wherein said sensor further comprises a source of DC bias.

9. The sensor as set forth in claim 1, wherein said membrane is functionalized with a polymer gel matrix.

10. The sensor as set forth in claim 1, wherein said sensor has a Q factor of at least about 50.

11. The sensor as set forth in claim 1, further comprising a plurality of reference elements, wherein each reference element includes:

a) an unfunctionalized membrane including a first electrode;

b) a substrate including a second electrode, wherein said first and second electrodes define a capacitor;

c) a support frame, wherein said support frame, said unfunctionalized membrane, and said substrate define a vacuum gap; and d) an electrical circuit including said capacitor, wherein said electrical circuit provides a reference output responsive to a mechanical resonance frequency of said reference element;

wherein said electrical circuit is configured to operate said reference element at or near an open circuit resonance condition.

12. The sensor as set forth in claim 11, wherein said resonance element is configured to operate at a mechanical resonance frequency that is the same as the mechanical resonance frequency of at least one sensor element.

13. The sensor as set forth in claim 1, wherein each of said sensor elements operates at a same or a different mechanical resonance frequency to another of said sensor elements.

14. The sensor as set forth in claim 1, wherein each of said sensor elements is functionalized with a same or different chemistry than another of said sensor elements.

15. The sensor as set forth in claim 1, wherein said sensor output is responsive to a fundamental mode and harmonics of said mechanical resonant frequency.

16. The sensor as set forth in claim 1, further comprising a source of heating said sensor element.

17. The sensor as set forth in claim 16, wherein said electrical circuit further provides a sensor output responsive to thermal desorption of bound agent from said functionalized membrane.

18. The sensor as set forth in claim 1, further comprising at least one thermistor.

19. The sensor as set forth in claim 1, further comprising at least one additional sensor, wherein said at least one additional sensor also contains a plurality of sensor elements.

20. A sensor comprising a plurality of sensor elements, wherein each of said sensor elements includes:
   a) a functionalized membrane;
   b) a substrate;
   c) a support frame, wherein said support frame, said functionalized membrane, and said substrate define a vacuum gap; and
   d) an electrical circuit, wherein said electrical circuit is configured to operate said sensor element at or near an open circuit resonance condition; and
   e) a detector, wherein said detector provides a sensor output responsive to a mechanical resonance frequency of said sensor element;

wherein said mechanical resonance frequency of said sensor element is responsive to binding of an agent to said functionalized membrane.

21. The sensor as set forth in claim 20, wherein said detector is an optical detector, a magnetic detector, a stress detector, or a capacitance detector.

* * * * *